United States Patent [19]

Cvitas et al.

[11] Patent Number: 4,789,469
[45] Date of Patent: Dec. 6, 1988

[54] APPARATUS FOR CONTINUOUSLY INTRODUCING OR REMOVING GASES INTO AND/OR FROM LIQUIDS

[75] Inventors: Vilim Cvitas; Karl Faltejsek, both of Linz; Gottfried Klinar; Reinhart Hanke, both of Leoben, all of Austria

[73] Assignee: Voest-Alpine Aktiengesellschaft, Linz, Austria

[21] Appl. No.: 1,641

[22] PCT Filed: Apr. 9, 1986

[86] PCT No.: PCT/AT86/00029

§ 371 Date: Dec. 4, 1986

§ 102(e) Date: Dec. 4, 1986

[87] PCT Pub. No.: WO86/06060

PCT Pub. Date: Oct. 23, 1986

[30] Foreign Application Priority Data

Apr. 9, 1985 [AT] Austria .............................. 1067/85

[51] Int. Cl.[4] .............................. C02F 3/18; B01F 3/04
[52] U.S. Cl. ..................................... 210/150; 210/179; 210/219; 261/92
[58] Field of Search .................... 210/150, 619, 198.1, 210/218, 219, 179; 261/92, 83, 91

[56] References Cited

U.S. PATENT DOCUMENTS

| 147,717 | 2/1874 | Warren | 366/327 X |
| 2,740,696 | 4/1956 | Longwell | 366/327 X |
| 3,684,458 | 8/1972 | McCammon et al. | 261/92 X |
| 3,761,059 | 9/1973 | Rothert et al. | 261/92 X |
| 4,101,384 | 7/1978 | Faust et al. | 261/92 X |
| 4,211,647 | 7/1980 | Fredman et al. | 210/619 X |
| 4,539,112 | 9/1985 | Durot et al. | 261/92 X |

FOREIGN PATENT DOCUMENTS

| 2625230 | 12/1976 | Fed. Rep. of Germany . |
| 1320157 | 3/1963 | France . |
| 1563514 | 4/1969 | France . |
| 2264584 | 10/1975 | France . |

Primary Examiner—Tom Wyse
Attorney, Agent, or Firm—Cushman, Darby & Cushman

[57] ABSTRACT

For the purpose of introducing or removing gases into liquids or out of liquids, in particular substrates being subject to a biological conversion, rotating plates (3) are immersed into the liquid phase. The plates (3) are rotatably arranged within a tubular receptacle (1) and arranged in at least one axial section such that they alternately include with the axis (2) of rotation extending in parallel relation to the liquid level an angle of more and less than 90°. Shut-off valves (9) for the gas supply conduit and for the gas discharge conduit are connected to the tubular container (1). The plates (3) are provided with a rough surface and are preferably formed of a porous, in particular foamed, material, wire mesh, wire grating or expanded metal sheet. (FIG. 1)

12 Claims, 2 Drawing Sheets

APPARATUS FOR CONTINUOUSLY INTRODUCING OR REMOVING GASES INTO AND/OR FROM LIQUIDS

BACKGROUND OF THE INVENTION

1. Field of the Invention

The invention refers to an apparatus for continuously introducing or removing or, respectively, for continuous adsorption and desorption of gases in liquids or from liquids, in particular of substrates being subject to a biological conversion, comprising a rotor being immersed into the liquid. The invention further refers to the use of such an apparatus for the aerobic and anaerobic conversion of substrates.

In the following, the term introducing or, respectively, removing gases into liquids or, respectively, from liquids is to comprise any type of continuous absorption or, respectively, desorption accompanied or not by a chemical conversion.

2. Description of the Prior Art

For the purpose of aerating or, respectively, gassing of liquids it is already known to immerse a number of nozzles below the liquid level. It is further known to provide rotating impellers for achieving a better mixing effect.

In connection with the biological conversion of substrates it has already become known to arrange the microorganisms on rotating discs which are cyclically immersed into the substrate to be converted and again are lifted out of the substrate. Such apparatuses already provide the advantage that the microorganisms could be allowed to regenerate themselves within a short time interval under conditions being different from that in the substrate. In this manner it was, for example, possible when using yeast in the fermentation process to regenerate the yeast in gases containing oxygen before the yeast was again introduced into the substrate to be subjected to a fermentation.

SUMMARY OF THE INVENTION

The invention now aims at providing an apparatus of the initially mentioned type which reliably allows to obtain an effective conversion of materials with the lowest possible energy expenditure and which furthermore reliably provides an agitation of the substrate allowing a connection between the existing biozenosis and the substrates and the nutrients without substantial diffusion pathes. For solving this task the invention essentially consists in that the rotor is rotatably supported within a tubular receptacle for rotation around an axis extending in essentially parallel relation to the surface of the liquid, that the rotor has plates non-rotatably connected with the rotor and arranged in transverse direction to said axis and at axially adjacent locations, the surface of said plates being of rough design, that axially adjacent plates include in at least one cross section comprising the axis alternately an angle of more and less than 90°, that the circumference of the plates is located at a distance from the inner surface of the tube and in that the tube has at least one liquid inlet, at least one liquid outlet as well as at least one gas inlet and gas outlet. On account of the rotor being rotatably supported within a tubular receptacle, a directional flow through the tube can be maintained and a continuous conversion reaction with fresh substrate or, respectively, fresh biomass can be obtained. On account of the rotor having non-rotatably connected thereto plates, which have a surface of rough design, in transverse direction relative to the axis and axially adjacent, a corresponding biomass can be adsorbed on the surface of these plates, and, above all, the fact that the plates arranged at axially adjacent locations include, in a section comprising the axis, an angle of alternately greater and smaller than 90° is responsible for obtaining within the tube a pulsating movement by means of which the liquid level can be risen and lowered in adjacent sections or to maintain a directional flow in case of correspondingly arranged overflow passages provided in the plates. The feature to rotatably support the plates in transverse direction to the axis of rotation and under an angle thereto deviating from 90° results in a particularly effective manner in a characteristic movement of the substrate being characterized by upwardly and downwardly directed streams as well as by transverse streams. Just these streams have as an effect that any gas offert from above the liquid level is sucked into the liquid so that the liquid is supplied with gas, in particular aerated, in a gentle manner and with the least possible energy expenditure. The tubular receptacle, which is subdivided into chambers, allows to seal the apparatus in a gas-tight manner by simple means, so that gaseous atmospheres of various types can be introduced till above the liquid level and can be sucked by the liquid on account of its movement, in particular its superficial movement. In this case, at least one liquid inlet, at least one liquid outlet as well as at least one gas inlet and at least one gas outlet is connected to the tube. The plates, which perform a wobbling movement on account of their orientation relative to the axis, exert to a certain degree a shearing effect on the liquid, said degree of shearing effect equally promoting a rapid reaction with a biozenosis adhering on the plates and prevents substantial diffusion pathes.

A distinctly improved biological conversion can be achieved if the plates are provided with bristles or the like or are made of porous, in particular foamed, material, wire meshes, wire grating or expanded metal sheet. In such an arrangement, substantial amounts of substrate are pressed through the plates in axial direction during each revolution of the plates and then again rinsed back in opposite direction, so that the biozenosis is regularly rinsed and cleaned. Simultaneously, new amounts of substrate are again and again brought to the microorganisms whereby the conversion can substantially be accelerated.

Simultaneously, the arrangement according to the invention provides the possibility to regenerate in time intervals the biological material by retracting same from the liquid, noting that by selecting a corresponding gas atmosphere a regeneration under oxydizing conditions as for example in case of yeast or a regeneration under a correspondingly adapted gas atmosphere can be effected.

Within adjacent areas of the receptacle there can be alternately performed an aerobic conversion and an anaerobic conversion, for which purpose it is, for example, sufficient to subdivide the tubular receptacle in axial direction into chambers by means of partition walls extending essentially in normal direction to the axis and having throttle cross-sections for the transport of matter between adjacent chambers. These throttle cross-sections serving for the transport of matter between adjacent chambers are located below the surface of the liquid, so that a gas-tight closure is obtained. Thus different gas atmospheres can be used in adjacent sections. The transport of the liquid medium can be effected by external pumps. In a particularly simple manner the arrangement can, however, be such that the plates have an essentially round or elliptical contour and are provided with overflow openings. Such overflow openings are immersed at least once below the liquid level on each revolution, so that, if there is provided a tight contact of the plates on the inner wall of the tubular receptacle, there results, on account of cyclically repeatedly lifting and lowering of the liquid level, an overflow from one chamber showing just the higher liquid level into an adjacent chamber showing just a lower liquid level. For this purpose, the maximum height of the liquid level within the chambers is conveniently limited to 20 to 60% of the internal diameter of the tubular receptacle.

The gas supply openings and the gas outlet openings can in a simple manner be connected in proximity of both front sides of the tubular receptacle above the maximum height of the liquid level. In dependence on the direction of flow of the liquid, the liquid can be gassed according to the principle of counter current, parallel current or crosscurrent. If there are arranged partition walls, the arrangement is advantageously such that the partition walls of the individual chambers are stationarily arranged and the overflow openings are arranged below the liquid level, preferably within the area located adjacent the inner mantle of the receptacle, and that separate gas supply openings and gas outlet openings are connected to each chamber and arranged in transverse direction to the axis of rotation.

The plates can be coated with microorganisms or with biomass for effecting a biological conversion. Biological conversions can be effected in connection with a sewage clarification in sewage clarifying plants as anaerobic and aerobic conversions. When subjecting sewage sludge to a fouling process, this process is most frequently an anaerobic process which provides methane, $CO_2$, clarifying plant gas or the like which can be removed from the respective chambers of such a receptacle. A number of anaerobically working microorganisms can substantially increase its activity if there is intermittently provided an aerobic phase which can be obtained by removing the bacteria from the liquid and introducing same into a corresponding gas atmosphere or by introducing air into the liquid at least in individual process steps. During the acetic acid fermentation there takes place, as a rule, an aerobic process which requires the introduction of air. In the continuous fermentation for producing ethanol by using yeasts enriched in sugar, the conversion per se is an anaerobic conversion. The efficiency of yeast can, however, substantially be increased if this yeast is cyclically subjected to an aeration.

The receptacle can advantageously be provided with heating means or cooling means.

The apparatus according to the invention is, in a particularly advantageous manner used for aerating liquids, in particular for aerobic conversions. The apparatus can, however, likewise be used for the continuous production of ethanol from a fermentable substrate or in general for anaerobic conversions such as fouling of sewage sludge or the like.

The apparatus according to the invention can advantageously be used for degassing purposes in connection with anaerobic conversions, in particular for the removal of $CO_2$ or for gently mixing substrate and biomass.

BRIEF DESCRIPTION OF THE DRAWING

In the following, the invention is further illustrated with reference to embodiments shown in the drawing in which.

DETAILED DESCRIPTION OF THE PREFERRED EMBODIMENTS

Figure 1:
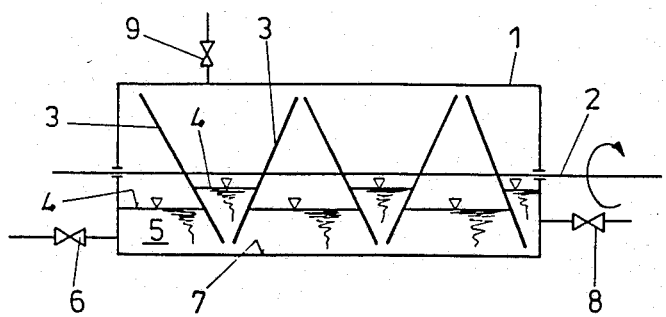
FIG. 1 is a schematic side elevation of an apparatus according to the invention.

FIG. 1 shows a tubular receptacle 1 within which a shaft 2 is rotatably supported. The shaft 2 carries a plurality of plates 3, which, according to the side elevation of FIG. 1 and, respectively, according to the axial section shown in FIG. 1, alternately include with the shaft 2 an angle of more than 90° and less than 90°. In this case, the corresponding angles are alternately oppositely equal. The plates are immersed into the liquid level 4 of a liquid 5, noting that the supply of liquid can be controlled by a shut-off valve 6. The inner wall of the tubular receptacle is designated by 7 and the outer circumference of the plates 3, which have a substantially round or elliptical contour in case of a tube having the diameter of a circle, is located at a small distance from the inner mantle 7 of the tubular container 1. During each revolution of the plates 3 together with the shaft 2, the liquid level 4 is alternately lifted and lowered if the throttle cross-section remaining between the circumference of the plates 3 and the inner wall 7 of the container is sufficiently small. Discharge of the liquid is controlled by a shut-off valve 8. The gas atmosphere can be introduced or removed according to the requirements via a valve 9. On account of the receptacle 1 being pressure-resistent, the arrangement can also be operated under a sub-atmospheric pressure.

In the representation according to FIG. 2 there are provided between adjacent chambers additional partition walls 10 being provided with overflow openings 11 below the liquid level 4.

Figure 2:
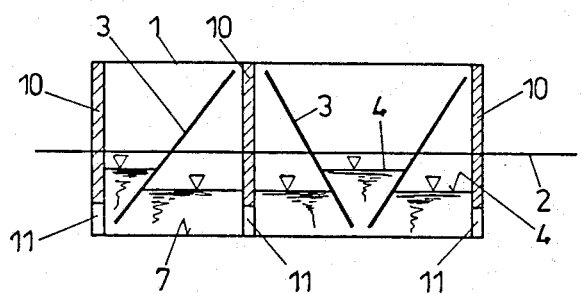
FIG. 2 is a partial view analogous to that of FIG. 1 and showing additional partition walls.
Figure 3:
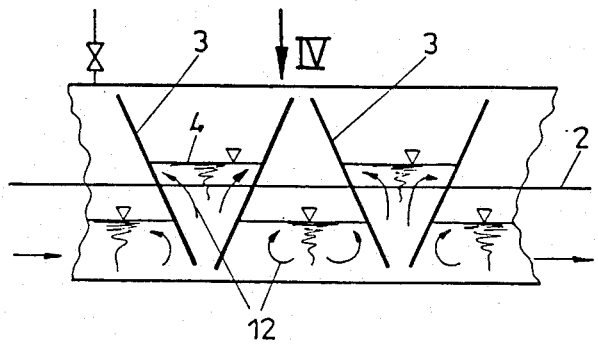
FIG. 3 and 4 illustrate the flow conditions within the liquid phase in a side elevation and, respectively, in the top plan view corresponding to the arrow IV of FIG. 3.
Figure 4:
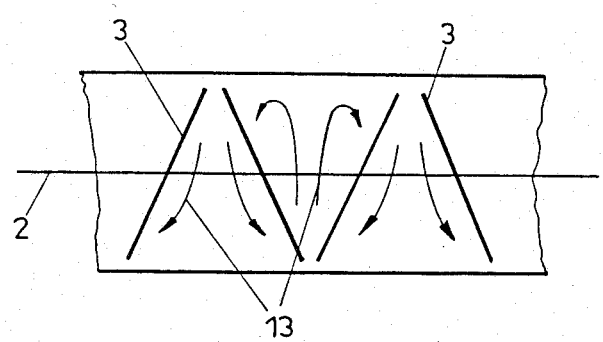

FIGS. 3 and 4 explain in detail the flow conditions in the liquid phase. In this case, FIG. 3 corresponds to the view shown in FIG. 1, and lifting and lowering, respectively, of the liquid level within adjacent chambers results in a corresponding flow in direction to the surface or away from the surface, as is shown in detail by the arrows 12. FIG. 4 shows the corresponding top plan view of the arrangement according to FIG. 2, and the transverse streams resulting on each revolution of the plates 3 are indicated by the arrows 13.

The plates 3 are, for the biological conversion, loaded with microorganisms and have for this purpose a rough surface. Preferred plates are plates of wire mesh or expanded sheet metal which provide a throttle resistance in axial direction. In such arrangements, lifting or lowering, respectively, of the liquid level in adjacent chambers is, of course, not very pronounced. On account of the flow conditions illustrated with FIGS. 3 and 4 there results, however, an axial stream extending through the plates 3, so that the substrate is intesely contacted with the microorganisms.

Figure 5:
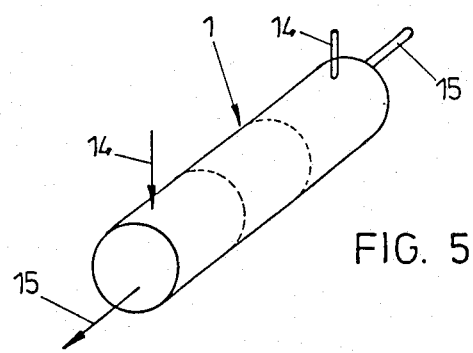
FIG. 5 shows in a perspective view a multi-chamber arrangement for aeration according to the parallel current principle or the counter current principle and FIG. 6 shows an arrangement comprising partition walls and a means for gassing or aerating, respectively, according to the crosscurrent principle.

In FIG. 5 there is shown a perspective view of a multi-chamber reactor and the supply openings and the discharge openings for gas are designated by 14. The liquid is supplied and discharged via the conduits 15. In dependence on the direction of supply of the gas, the gas can be passed relative to the flow direction of the liquid according to the countercurrent principle or according to the parallel current principle.

Figure 6:
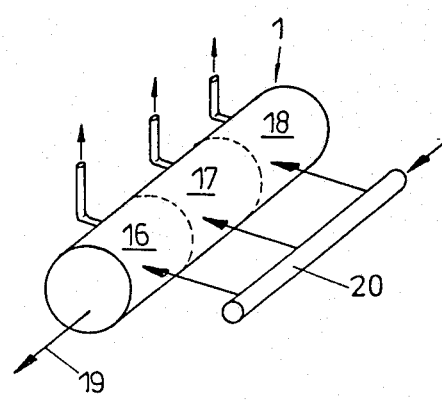

In the arrangement according to FIG. 6 the operation is selected according to the crosscurrent principle, noting that between the individual sections 16, 17 and 18 of the tubular receptacle 1 there are provided partition walls 10 as they are shown in FIG. 2. These partition walls 10 have overflow openings 11 below the liquid level and the gas flows in each of the individual chambers 16, 17 and 18 in transverse direction relative to the flow direction, which is indicated by the arrow 19, of the liquid. Different or identical gases may be introduced into the individual chambers. In the representation according to FIG. 6, the gas is supplied via a manifold 20 so that each chamber receives the same gas.

What is claimed is:

1. Apparatus for introducing or removing gases into liquids or from liquids, in particular substrates being subject to a biological conversion, comprising a rotor rotatably supported within a horizontal tubular receptacle for rotation around a rotation axis extending in essentially parallel relation to the surface of a liquid in the receptacle, the rotor having plates non-rotatably connected with the rotor and arranged in transverse direction to said rotation axis and at axially adjacent locations, said plates being partially but not wholly immersed in the liquid in the tubular receptacle, the surface of said plates being rough, and axially adjacent plates having in at least one section comprising the rotation axis alternately an angle of more and less than 90°, the circumference of the plates being shaped relative to and spaced from the inner surface of the receptacle a small distance such that the space throttles liquid flow therethrough with the result that, upon rotation of the rotor about said rotation axis, the liquid level between adjacent plates is alternately lifted and lowered, the receptacle having connected thereto at least one liquid inlet, one liquid outlet, and at least one gas inlet and gas outlet.

2. Apparatus as in claim 1 wherein the plates are provided with bristles.

3. Apparatus as in claim 1 wherein the plates are formed of a porous material such as a foamed material, wire mesh, wire grating or expanded metal sheet.

4. Apparatus as in claim 1 wherein the tubular receptacle is subdivided in axial direction into chambers by partition walls.

5. Apparatus as in claim 4 wherein the partition walls are oriented substantially normal to said rotation axis and have throttle cross sections for the transport of matter between adjacent chambers.

6. Apparatus as in claim 1 wherein the plates have an essentially elliptical contour and are provided with overflow openings.

7. Apparatus as in claim 1 wherein the height of the liquid level within the chambers is limited to 20 to 60 percent of the inner diameter of the tubular receptacle.

8. Apparatus as in claim 1 wherein the gas inlet and gas outlet are connected in proximity to both front sides of the tubular receptacle above the maximum height of liquid level.

9. Apparatus as in claim 1 wherein the tubular receptacle is subdivided in the axial direction into chambers by partition walls which are stationarily arranged and comprise overflow openings below the height of the liquid level, each chamber having separate gas supply openings and gas discharge openings arranged in transverse relation to said rotation axis.

10. Apparatus as in claim 9 wherein the overflow openings in the partition walls are located near the inner surface of the tubular receptacle.

11. Apparatus as in claim 1 wherein the plates are coated with microorganisms or biological mass.

12. Apparatus as in claim 1 wherein the tubular receptacle is equipped with heating or cooling means.

* * * * *